United States Patent [19]

Kranz et al.

[11] Patent Number: 5,057,110
[45] Date of Patent: Oct. 15, 1991

[54] INTRAMEDULLAR NAIL

[75] Inventors: Curt Kranz, Berlin; Hanns Seiler, Wadgassen, both of Fed. Rep. of Germany

[73] Assignee: Johnson & Johnson, New Brunswick, N.J.

[21] Appl. No.: 442,795

[22] Filed: Nov. 29, 1989

[30] Foreign Application Priority Data

Dec. 1, 1988 [DE] Fed. Rep. of Germany ....... 3840798

[51] Int. Cl.⁵ .............................................. A61F 5/04
[52] U.S. Cl. ......................................... 606/62; 606/67
[58] Field of Search ...................... 606/62, 63, 64, 65, 606/67, 68, 76, 77, 78, 104

[56] References Cited

U.S. PATENT DOCUMENTS

| 2,511,051 | 6/1950 | Dzus | 606/104 |
| 2,952,254 | 9/1960 | Keating | 606/67 |
| 4,040,129 | 8/1977 | Steinemann | 606/76 |
| 4,164,794 | 8/1979 | Spector | 606/76 |
| 4,375,810 | 3/1983 | Belykh | 606/62 |
| 4,495,664 | 1/1985 | Blanquaert | 606/62 |
| 4,599,085 | 7/1986 | Riess | 606/76 |
| 4,711,234 | 12/1987 | Vives | 606/63 |
| 4,733,654 | 3/1988 | Marino | 606/62 |
| 4,756,307 | 7/1988 | Crowninshield | 606/67 |
| 4,776,329 | 10/1988 | Treharne | 606/77 |
| 4,827,917 | 5/1989 | Brumfield | 606/62 |
| 4,858,603 | 8/1989 | Clemow | 606/77 |

FOREIGN PATENT DOCUMENTS

| 0260222 | 3/1988 | European Pat. Off. . |
| 3537318 | 9/1986 | Fed. Rep. of Germany . |
| 2146535 | 4/1985 | United Kingdom . |
| 88/01849 | 3/1988 | World Int. Prop. O. . |

Primary Examiner—Robert A. Hafer
Assistant Examiner—Michael Brown
Attorney, Agent, or Firm—Spencer & Frank

[57] ABSTRACT

An intramedullar nail for the treatment of fractures of long tubular bones, made of a shaft having a nail tip and at least one fixation screw. A portion of the nail tip is made of absorbable material. The fixation screws penetrate the bone and a section of the nail, causing the bone and nail to be attached.

9 Claims, 1 Drawing Sheet

INTRAMEDULLAR NAIL

CROSS REFERENCE TO RELATED APPLICATION

This application claims the priority of the Federal Republic of Germany application No. P 38 40 798.1 filed Dec. 1, 1988, which is incorporated herein by reference.

BACKGROUND OF THE INVENTION

The present invention relates to an intramedullary nail which is fixable by means of locking screws for the operative treatment of fractures of long tubular bones and a device to carry out the method.

The intramedullary nail first introduced by Küntscher in 1940 is today one of the most widely used methods for the operative treatment of fractures of long tubular bones. Some of the advantages over other methods are: stable fixation of the fracture ends due to the internal bone splint; no operative opening of the fractured area, small risk of infection, short period of bedrest, the patient can get up earlier without a plaster cast and a post-treatment is not necessary as muscular atrophy does not occur due to the patients freedom of movement.

The locking of the intramedullary nail is necessary for all fractures of the shaft as these remain unstable after normal intramedullar nailing. In the case of pseudarthrosis the proximal and the distal fragments are locked after the fracture has been located.

The problem with the locking screw is that it is difficult to find the bore holes for the locking screws in the intramedullary nail as the nail can bend while it is being inserted into the bone. An x-ray manipulator must be used to relocate the bore holes in such cases.

SUMMARY OF THE INVENTION

It is an object of the invention to eliminate, to a great extent, the disadvantage described above and to provide devices which make it easier to lock the intramedullary nail. Another object of the invention is to minimise the amount of x-ray radiation the patient receives, in the interest of the patient, by no longer requiring the x-ray manipulator.

The above and other objects are accomplished according to the invention by an intramedullary nail in which a part of the nail up made of a material which is totally absorbable by the body. This means that one does not, any longer, need to prebore that part of the intramedullary nail which is absorbable. The holes are bored for fixation screws after the intramedulary nail has been inserted into the bone. The shavings that are produced are not harmful as they can be transformed into bodily substance. As there is no longer any need to locate the bore holes neither the x-ray manipulator nor the sighting device are required.

Certain fractures of the femur and the tibia require that the intramedullary nail is locked in the upper part which does not consist of absorbable material. The locking is not problematic since the position of the prebored holes can be easily ascertained from the position of the intramedullar nail.

In an advantageous embodiment of the invention, at least one of the locking screws is itself made of absorbable material. The locking screws used to lock the nail tip, which consists of an absorbable material, should preferably also be of absorbable material, as in this case post-operative surgery is not required to remove the locking screw. An absorbable material which can be used is, for example, the tried and tested polylaced.

The firm joining together of the two parts of the intramedullar nail is, in a preferred embodiment of the invention, carried out using a non-rusting cover which is pushed over the ends to be joined and then clamped. It is appropriate to make the length of absorbable material of the intramedullar nail as long as the intended locking length. In this way a high stability and durability can be guaranteed up until the fracture has fully healed.

The total length of the intramedullar nail is not critically critically since the absorbable part of the nail can be longer than actually required as this does not lead to any complications. The metallic part of the intramedullar nail on the other hand, should be kept as short as possible. After the fracture has healed only the metallic parts of the implant are removed. The absorbable part has, in the meantime, shrunk to such an extent due to the transformation into bodily substance that the mechanical joining device, for example a cover, can no longer hold the nail and therefore only the metallic parts of the intramedullar nail need to be removed.

As a wire carrier is used to insert the intramedullar nail into the bone the nail is bored concentrically throughout its whole length.

DESCRIPTION OF THE PREFERRED EMBODIMENT

Figure 1:
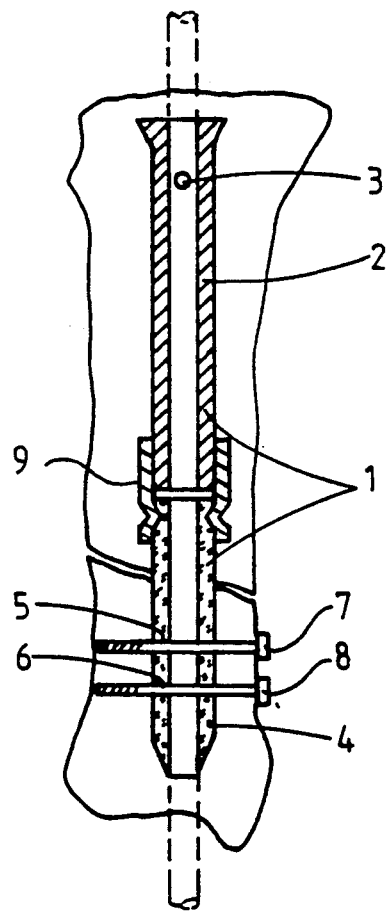
FIG. 1 is a sectional view of a preferred embodiment of an intramedullar nail with a partially indicated distal fracture.

The concentrically bored intramedullar nail 1 is inserted into the bone marrow using a medullary canal reamer and a wire carrier ( indicated with phantom lines). The wire carrier is then removed from the bone. The intramedullar nail 1 has a bore 3 on its upper side 2 into which a fixation screw is inserted after location using a sighting device. The nail tip 4 consisting of absorbable material is only bored open at the areas 5 and 6 after the intramedullar nail has been inserted into the bone. The shavings that are produced during boring are not problamatic and do not need to be removed as they are also of absorbable material.

The insertion in of the absorbable fixation screws 7 and 8 can be done without needing to measure out and set the screwing position as these are not prebored holes which need to be located by means of radiation.

The nail head 2 and the nail tip 4 are joined tightly together by a thin-walled cover 9. This cover 9 is pushed over the two parts of the intramedullary nail to be joined and then moulded. In the preferred embodiment the absorbable parts of the intramedullar nail and the fixation screws 7 and 8 are of polylacted and the cover is of titanium or a titanium alloy.

The two parts of the intramedullar nail are connected together just above the area with the fixation screws 7 and 8. Stability is thereby guaranteed until the bone parts have grown back together. After complete healing all the parts of the implantate are removed, apart from the absorbable nail tip and the absorbable fixation screws 7 and 8 which have dissolved for the most part already.

It will be understood that the above description of the present invention is susceptible to various modifications, changes and adaptations, and the same are intended to be comprehended within the meaning and range of equivalents of the appended claims.

What is claimed is:

1. An intramedullar nail, having a tip section constituting the tip of the nail for operative treatment of fractures of a long tubular bone, the nail being fixable by means of fixation screws, said nail tip section consisting of an absorbable material, said tip section having fixation screws passing therethrough in order to attach the nail to the bone.

2. An intramedullar nail as defined in claim 1, wherein at least one of said fixation screws consist of an absorbable material.

3. An intrameddular nail as defined in claim 1, wherein said absorbable material is polylactid.

4. An intrameddullar nail as defined in claim 1, wherein the nail has a metallic head, further comprising a cover which connects the nail tip firmly with the metallic nail head.

5. An intramedullar nail as defined in claim 4, wherein said cover consists of a member of the group consisting of titanium and a titanium alloy.

6. An intramedullar nail as defined in claim 1, wherein the absorbable nail tip section ends directly above an area in which said fixation screws are inserted.

7. An intramedullar nail as defined in claim 1, wherein said nail has a concentric bore which extends throughout its whole length.

8. An intramedullar nail, having a tip section constituting the tip of the nail for operative treatment of fractures of a long tubular bone, said nail tip section consisting of an absorbable material.

9. An intramedullar nail for operative treatment of fractures of a long tubular bone, comprising a shaft having a nail tip, said nail having a tip section consisting of absorbable material and at least one fixation screw which penetrates the bone and said tip section, whereby the bone and nail are attached.

* * * * *

UNITED STATES PATENT AND TRADEMARK OFFICE
CERTIFICATE OF CORRECTION

PATENT NO. : 5,057,110

DATED : October 15, 1991

INVENTOR(S) : Curt Kranz

It is certified that error appears in the above-identified patent and that said Letters Patent is hereby corrected as shown below:

Claim 3, column 3, line 18, "intrameddular" should read --intramedullar--.

Claim 4, column 3, line 21, "intrameddular" should read --intramedullar--.

Signed and Sealed this

Fourteenth Day of September, 1993

Attest:

BRUCE LEHMAN

Attesting Officer

Commissioner of Patents and Trademarks